(12) United States Patent
Mutch et al.

(10) Patent No.: US 10,656,045 B2
(45) Date of Patent: May 19, 2020

(54) APPARATUS FOR ANALYZING THE PERFORMANCE OF FLUID DISTRIBUTION EQUIPMENT

(71) Applicants: Kathleen Mary Mutch, Tempe, AZ (US); Richard Laszlo Madarasz, Tempe, AZ (US)

(72) Inventors: Kathleen Mary Mutch, Tempe, AZ (US); Richard Laszlo Madarasz, Tempe, AZ (US)

(*) Notice: Subject to any disclaimer, the term of this patent is extended or adjusted under 35 U.S.C. 154(b) by 218 days.

(21) Appl. No.: 15/853,823

(22) Filed: Dec. 24, 2017

(65) Prior Publication Data
US 2018/0202890 A1    Jul. 19, 2018

Related U.S. Application Data

(60) Provisional application No. 62/447,271, filed on Jan. 17, 2017.

(51) Int. Cl.
*G01M 3/28* (2006.01)
*G08B 21/18* (2006.01)
(Continued)

(52) U.S. Cl.
CPC ............ *G01M 3/28* (2013.01); *F17D 5/02* (2013.01); *G01F 1/00* (2013.01); *G01F 23/00* (2013.01);
(Continued)

(58) Field of Classification Search
CPC ...... G01M 3/28; G01F 23/18; G01L 19/0092; G01N 33/1826; G08B 21/18; G08B 21/182
See application file for complete search history.

(56) References Cited

U.S. PATENT DOCUMENTS

| 4,796,466 A | 1/1989 | Farmer |
| 613 A | 4/1989 | Stello et al. |

(Continued)

FOREIGN PATENT DOCUMENTS

| CN | 106680574 A1 | 5/2017 |
| CN | 106817398 A1 | 6/2017 |

(Continued)

OTHER PUBLICATIONS

Madarasz, Mutch, "Continuous Performance Monitoring of Elevators", Elevator World, Aug. 2008, p. 80-84. (description of QarVision Remote Elevator Diagnostic System).
(Continued)

*Primary Examiner* — Ryan A Reis

(57) ABSTRACT

The present invention is a performance analysis apparatus for fluid distribution equipment that operates independently of the control system of the fluid distribution equipment to automatically determine when equipment is not functioning correctly. It comprises an analyzer computer, one or more sensor sets, and a computer program. The sensor sets are connected to the analyzer computer and comprise sensors for measuring physical properties of fluid distribution equipment. The computer program reads configuration data from data files to determine the types of fluid distribution equipment that are being collectively analyzed and the sensor sets that are present, repetitively requests raw physical measurements from the sensor sets, computes the physical properties of the fluid distribution equipment from the raw physical measurements, analyzes the physical properties to find abnormalities, sends warnings and status, and stores the results and times of the analysis computations in data files in the electronic storage.

37 Claims, 9 Drawing Sheets

(51) Int. Cl.
*G01F 23/18* (2006.01)
*G01R 21/06* (2006.01)
*G01N 33/18* (2006.01)
*G01K 13/00* (2006.01)
*G01L 19/00* (2006.01)
*G01F 1/00* (2006.01)
*G01F 23/00* (2006.01)
*G01L 13/00* (2006.01)
*G01M 3/02* (2006.01)
*F17D 5/02* (2006.01)

(52) U.S. Cl.
CPC .......... *G01F 23/18* (2013.01); *G01K 13/00* (2013.01); *G01L 13/00* (2013.01); *G01L 19/0092* (2013.01); *G01M 3/02* (2013.01); *G01N 33/18* (2013.01); *G01N 33/1826* (2013.01); *G01R 21/06* (2013.01); *G08B 21/18* (2013.01); *G08B 21/182* (2013.01)

(56) References Cited

U.S. PATENT DOCUMENTS

| | | | |
|---|---|---|---|
| 4,830,757 A * | 5/1989 | Lynch | G01N 33/18 210/104 |
| 4,999,117 A | 3/1991 | Palmu et al. | |
| 5,739,420 A | 4/1998 | Peterson | |
| 5,870,140 A | 2/1999 | Gillberry | |
| 6,353,804 B1 | 3/2002 | Bowman | |
| 6,567,709 B1 | 5/2003 | Malm et al. | |
| 6,691,068 B1 | 2/2004 | Freed et al. | |
| 6,753,186 B2 | 6/2004 | Moskoff | |
| 6,764,019 B1 | 7/2004 | Kayahara et al. | |
| 7,139,564 B2 | 11/2006 | Herbert | |
| 7,357,034 B1 | 4/2008 | Worthington | |
| 7,398,184 B1 | 7/2008 | Chen | |
| 7,818,071 B2 | 10/2010 | Hartkamp et al. | |
| 9,134,160 B2 | 9/2015 | Ahmad et al. | |
| 9,568,391 B2 | 2/2017 | Linford et al. | |
| 9,785,142 B2 | 10/2017 | Kwak | |
| 9,797,785 B2 | 10/2017 | Giorgi et al. | |
| 10,030,818 B2 * | 7/2018 | Hoskins | E03B 7/00 |
| 2005/0093191 A1 | 5/2005 | Gardener | |
| 2009/0000381 A1 | 1/2009 | Allison et al. | |
| 2009/0105969 A1 | 4/2009 | Saylor | |
| 2009/0115424 A1 | 5/2009 | King et al. | |
| 2010/0332149 A1 * | 12/2010 | Scholpp | C02F 1/008 702/25 |
| 2011/0215945 A1 * | 9/2011 | Peleg | G01M 3/2807 340/870.02 |
| 2012/0215464 A1 | 9/2012 | Daubney | |
| 2012/0232750 A1 | 9/2012 | Leigh | |
| 2014/0297210 A1 * | 10/2014 | Kamel | H02J 13/0006 702/62 |
| 2015/0365303 A1 | 12/2015 | Lloyd | |
| 2017/0117064 A1 | 4/2017 | Lepine et al. | |

FOREIGN PATENT DOCUMENTS

| | | |
|---|---|---|
| KR | 20170040478 A1 | 4/2017 |
| WO | WO2017138948 A1 | 8/2017 |

OTHER PUBLICATIONS

Qameleon Technology, Inc., "SpikeWatcher", product brochure, pp. 1-2, Mar. 28, 2016, Tempe, AZ.

* cited by examiner

APPARATUS FOR ANALYZING THE PERFORMANCE OF FLUID DISTRIBUTION EQUIPMENT

BACKGROUND OF THE INVENTION

The present invention is in the technical field of fluid distribution equipment. More particularly, the present invention is in the technical field of equipment performance monitoring and analysis of fluid distribution equipment.

A significant part of America's infrastructure concerns the transport and distribution of fluids. These long-distance distribution systems include municipal water utilities, wastewater systems, petroleum pipelines, and agricultural irrigation systems. There are also many short-distance systems, such as those used in oil refineries, water treatment plants, wastewater facilities, chemical plants, and even area-wide heating and cooling facilities. These distribution systems are comprised of different types of equipment, such as pipes, valves, pumps, storage tanks, wells, filters, sensors, and control systems. Sometimes these systems are operated by automated supervisory control and data acquisition (SCADA) systems. Other systems are operated manually by humans that may be located remotely.

These systems are critical to the country's health, security, and economy. Yet they are all subject to failures. They are expensive to build, operate, and maintain. The construction cost of a new pump station can be from $100,000 to over $1B, in 1999 dollars. The EPA estimates that energy usage accounts for 85 to 95% of the cost of operating a pump station. The cost of maintaining the equipment can be 3 to 15% of the pump station annual cost. The failure of a water or sewer main can easily result in millions of dollars for repair. These costs will be much higher if the fluid is gasoline or a hazardous chemical. Due to the high cost of building new infrastructure, the preferred strategy is to increase the efficiency of the equipment and to extend the lifetime of the equipment as long as possible.

Pipeline failures can usually be attributed to one of three causes: 1) accidental damage from collisions or construction equipment, 2) corrosion, 3) incorrect operation of connected equipment by human or automated control.

Accidental damage usually results in a catastrophic break in the pipe. This can be detected by a rapid decrease in pressure or flow through the pipe. This is a very rare occurrence and requires constant monitoring of the pipes. The process either generates a lot of data that must be transmitted and analyzed, or often results in a delay in response due to long sampling intervals.

The following patents cover systems and methods for detecting catastrophic failures in pipelines:

U.S. Pat. No. 4,796,466 discloses a system for monitoring pipelines. This is a computerized system that uses statistical techniques to continuously analyze a pipe to detect a rapid decrease in pressure or flow. The system does not record data, but instead, outputs a signal that can be used to notify operators of a problem.

U.S. patent application No 20090115424 discloses an apparatus and method for detecting faults in tanks. It measures the length of time that a pump runs to fill the tank. If there is a significant difference in the length of the pump cycle, a warning is issued.

Corrosion happens over a long period of time, resulting in slow leakage until a catastrophic failure occurs. This is often detected by monitoring a gradual decrease in pressure over a long period of time.

The following patents cover systems and methods for detecting small leaks in pipelines and other equipment:

U.S. Pat. No. 9,134,160 discloses an online multi-phase flow meter system. This system continuously measures the volume of water, gas, and oil flowing concurrently in a pipeline. The system continuously adjusts for differences in flow rate to maintain consistent sampling.

U.S. Pat. No. 5,739,420 discloses a system for detecting ground water infiltration. The system looks for leaks in a pipeline by inserting a probe into the pipe at manholes and tracking its location from the surface of the ground. Properties are recorded at different geographic locations and later analyzed.

U.S. patent application No 20120232750 discloses a system to monitor the transport of fluids. The device continually monitors the level and pressure of fluid in a truck-mounted tank. Measurements are recorded including time and geographic location to determine if leaks have occurred.

Incorrect operation of connected equipment, such as valves and pumps, can cause stresses that are not immediately damaging. Opening and closing a valve in the system can cause very rapid changes in pressure (known as transient pressures) which may be outside of the design safety limits of the equipment. These changes can last from a few milliseconds to several minutes. These transients can also be caused by power failures that result in rapid shutdown of pumps. Either of these cases can be caused by human operators or a failure in the control system. Typical SCADA systems do not sample fast enough to detect these changes in pressure. In addition, the problem may actually be better detected by monitoring the quality of the power going to the equipment.

The following patents cover systems and methods for detecting transient pressures in pipelines:

U.S. Pat. No. 7,357,034 discloses a dynamic transient pressure detection system. This is an apparatus that continuously monitors pressures in pipelines and containment vessels. The pressure is recorded at a low speed and each sample is statistically examined for a deviation from the normal pressure. When a transient is detected, the recording speed is increased. When the pressure is no longer determined to be part of a transient, the recording rate is returned to a slow speed. Analysis of the data is performed manually.

U.S. Pat. No. 9,568,391 discloses a pipeline monitoring unit and method. This apparatus is used to detect transient pressures in pipelines. The unit measures the pressure at a high sample rate and statistically determines if it is part of a transient. If it is, it is recorded at the sampling speed. If it is not part of the transient, periodic samples of the pressure are recorded at a slower speed. The data are analyzed remotely.

U.S. patent application No 20090000381 discloses an acoustic impact detection and monitoring system. This system inserts multiple hydrophones into a pipeline to detect abrupt sounds, which may be an indication of a pressure transient. The system calculates the time of arrival at the different hydrophones to attempt to locate the source of the transient.

Failures can also occur in equipment such as pumps and valves, just as they do in pipelines. Mechanical wear and stresses are more likely to occur than damage from corrosion. Catastrophic pump failures can be determined by monitoring pressure and flow rate, just as in pipes. But detecting conditions that cause these failures usually requires monitoring over long periods of time. Increases in bearing temperature, current draw, and vibration are indications of a potential failure. Electrically and hydraulically operated valves have similar problems and can be monitored in the same way.

The following patents cover systems and methods for monitoring and control of machinery:

U.S. Pat. No. 6,567,709 discloses an integrated monitoring, diagnostics, shutdown, and control system. This system remotely monitors the condition of rotating machinery. It uses multiple sensors to determine a control output to be sent to the machine controller. The parameters of the machine controller are altered automatically.

U.S. patent application No 20050093191 discloses a system and method for monitoring the operation of an injection molding machine. While not equipment used in fluid distribution, it does include the operation of pumps and valves. The system measures pressure and flow rate in the injection cylinder. The system analyzes the sensor readings, calculates appropriate control parameters, and adjusts the machine accordingly.

U.S. patent application No 20090105969 discloses a method and device for the assessment of fluid collection networks. This apparatus is used to monitor the fluid flow in an open-channel distribution network, such as a sewer system. An accelerometer and a pressure sensor are installed on a float that rides on top of the fluid. The readings are recorded for later analysis.

Chinese Pat. No CN106680574 (A) discloses a system to sense over-voltage conditions in electrical substation equipment. The system independently uses sensors to monitor the conditions in transformers. These readings are compared to results of simulation and waveform analysis to determine if the equipment has reached the end of its useful life.

U.S. Pat. No. 4,999,117 discloses an apparatus and method to monitor a wastewater pump station. The performance of the pump station equipment is determined by measuring the change in the level of fluid in the wet well over time, during periods when the pump is running and when it is not running. The differences in changes are compared to known performance levels and alarms are issued as appropriate.

Failures in electronic control systems (SCADA) are much harder to detect, but can lead to the same failures in equipment. The control system may fail to send signals to the equipment, or may be sending inappropriate signals. This could be the result of control failure, incorrect control programs, or intentional malicious actions. The only way to detect these problems is to monitor the actual performance of the end system.

The following patents cover systems and methods for monitoring control systems:

U.S. Pat. No 6,764,019 discloses a method for servicing and maintaining heat supply equipment. This method uses a computer connected to a boiler control system that sends data to a remote computer for display and analysis. Maintenance personnel evaluate the data and make decisions.

Korean Pat. No. KR20170040478 (A) discloses an apparatus for life evaluation of pump mechanical seals. The apparatus collects data from sensors connected to the pump and compares the readings to a simulation of the pump seal under various conditions. This is for quality testing during manufacturing and not for monitoring fielded equipment.

Chinese Pat. No CN106817398 (A) discloses an embedded equipment monitoring and alarm system. This system is built into an industrial controller to monitor a process. The results of the monitoring are sent back to the controller to adjust its operation. This is not an independent monitoring system.

U.S. Pat. No. 9,797,785 discloses a method for monitoring environmental conditions. This is a system for monitoring the conditions in a climate-controlled environment. Sensors are located in the environment, such as a cold storage facility, and the readings are sent to a remote location for analysis. Alarms are displayed at the remote site.

U.S. patent application No 20150365303 discloses a method for analyzing SCADA systems. This system uses independent computers to capture the outputs of a SCADA system. The outputs are compared to the design specifications of the system to determine if the system is installed correctly. It does not monitor the actual operation of the SCADA system in use.

U.S. Pat. No. 9,785,142 discloses an apparatus and system for data processing in SCADA systems. This system gets the current readings from the SCADA system and determines the state of the equipment by comparing to a library of known states. Alarms are determined from the state. This system monitors the state of the whole installation, but is not independent of the control system.

International patent application No WO2017138948 (A1) discloses a method to automatically set parameters of process monitoring equipment. This method uses simulation of production processing equipment to set the control limits of the monitoring systems. The simulations predict the degradation of the equipment over time and calculate how the monitoring equipment should be modified. This is not a control system, but is used to configure the control equipment.

U.S. Pat. No. 6,353,804 discloses a method of statistically predicting equipment performance. The method consists of entering data collected from a mechanical device into a simulation of the device to create a set of equations specific to the equipment. These equations are used to generate a probability of the equipment's performance. This is not a monitoring system, but is used to evaluate performance based on measurements.

The QarVision Remote Elevator Diagnostic System by Qameleon Technology, Inc. is an example of a monitoring and diagnostic system that operates independently of a control system to analyze the performance of machinery. QarVision uses its own sensors to determine if an elevator is behaving in a way that the controller should be telling it to. It is a stand-alone, self-contained equipment analyzer that issues reports and alarms directly to maintenance personnel.

Reducing the consumption of energy will have the biggest impact on the cost of operating a fluid distribution system. Energy consumption is easily measured with power metering equipment. However, determining the relationship between energy and the efficiency of the complete system is not easy. Other factors that can affect the energy consumption in a system include obstructions in pipes which cause pressure increases, clogged air relief valves that reduce flow rate due to air in pipes, and fluctuations in incoming voltage that cause motors to run erratically.

The following patents cover systems and methods for monitoring system costs:

U.S. Pat. No. 7,398,184 discloses a system for analyzing equipment performance and optimizing operating costs. This system uses sensors to determine the level of corrosion in equipment and determine its effect on the life of the equipment. This information is used to determine the lifetime cost of operating the equipment.

U.S. patent application No 20120215464 discloses a system to monitor energy consumption. The system combines sensors with readings from power meters to determining the cost of energy being used. These readings are compared to predetermined limits for making decisions.

Very often determining how well a complex system is performing involves the use of multiple sensors that take measurements from different pieces of equipment and performing analysis of the total system. Most monitoring systems limit themselves to a single parameter, such as the pressure in a pipeline, when the actual cause of a problem may come from an entirely different source. The complete fluid distribution system could itself be considered one entity.

The following patents cover systems and methods for monitoring entire systems:

U.S. patent application No 20170117064 discloses a system for collecting data from a nuclear power plant. The system communicates information for control computers, sensors, workers' hand-held devices, and operational documents to a remote site. A computer at the remote site evaluates the data, and generates reports which are sent back to the plant. This is not a self-contained or real-time system.

U.S. Pat. No. 6,753,186 discloses a system and method for monitoring water quality. The system utilizes chemical analysis equipment at residences within a water system. The water quality is determined and generates local alarms if there is a problem. These measurements are also transmitted to a central monitoring station where readings from multiple residences are analyzed. This provides an overall measure of the water system's operation.

U.S. statutory invention registration No H613 discloses a portable shipboard gunnery diagnostic apparatus. This device is used to determine the effectiveness of a gun to hit a remote target. The system uses sensors at the gun to measure velocity and information communicated from the target area. The measurements are analyzed to recommend to the crew how to better operate the gun.

U.S. Pat. No. 7,139,564 discloses a wireless communication device for field personnel. The device, such as a personal digital assistant or laptop computer, is used by field personnel to enter information about the operation of an HVAC system. This information may include readings from instruments, visual information about the equipment, and customer information. This is sent to a central computer for logging and analysis. The results are sent back to the field personnel. This system does not involve automatic collection of sensor measurements.

U.S. Pat. No. 7,818,071 discloses a method for controlling and/or optimizing production of oil and gas wells. The system collects sensor data for wells, pipelines, seismic monitoring equipment, and other sources, and sends them to a central location. The data are analyzed by a team of experts that makes recommendations for controlling processes at the remote facilities. These instructions are then sent back to the remote facilities. This is not an automated process.

Data logging systems are widely used to monitor equipment, including fluid distribution equipment. They usually consist of one or more sensors connected to a small computer that records raw data in an internal memory. Some of these systems have a means to transfer data to another device, such as a laptop computer. Others may have a means to communicate with a remote system. While most use traditional sensors, there are systems that have unique mechanisms for collecting information.

The following patents cover systems and methods for data collection and recording:

U.S. Pat. No. 5,870,140 discloses a system for remote meter viewing and reporting. This is a system that uses a camera to take images of a physical meter, such as a power meter, and then sends the image to a remote computer for analysis. The remote computer converts the image to a measurement which is used to create a customer bill. The data being stored and communicated are the raw pixels from the camera.

U.S. Pat. No. 6,691,068 discloses an apparatus and method for obtaining process data. This device is a sensing and data storage system built on a silicon wafer that is loaded into processing equipment. The device takes measurements of the process which can be later analyzed to optimize the wafer production parameters. This is an independent, in-situ device with communication capabilities.

The SpikeWatcher Change Detection System by Qameleon Technology, Inc. is an independent device that combines transient signal detection with long-term, multiple sensor recording. It has the ability to communicate with external devices and systems using the interne and wired or wireless communication mechanisms. It also has the ability to be reconfigured remotely for different purposes in the same installation. A technician may decide to focus the monitoring on power consumption for a period of time and then switch the focus to vibration and temperature. However, this system only records data. Any analysis must be performed at a remote site using manual and programmatic means.

The need exists for a system to continually monitor and analyze equipment in critical infrastructures. The system needs to be independent of the existing equipment and any control system, focusing instead on the actual performance of the equipment. It should be easy to install in remote locations without interfering with the fluid distribution system itself. It should be self-contained, able to operate autonomously for long periods of time, be tolerant to failures in communications and power, and be resistant to electronic attacks. The Apparatus for Analyzing the Performance of Fluid Distribution Equipment described herein addresses these needs.

BRIEF SUMMARY OF THE INVENTION

The present invention is an apparatus for analyzing the performance of fluid distribution equipment. Such fluid distribution equipment includes, but is not limited to: fresh water collection, treatment and delivery systems; wastewater collection and treatment systems; petroleum pipelines, drilling systems, and refineries.

The invention functions independently from the control system of the fluid distribution equipment. It analyzes sensor data to determine the equipment's actual performance. The control system of the fluid distribution equipment issues commands to various components, such as pumps and valves. The invention measures and analyzes what the components are actually doing, without knowing the commands that were issued.

The invention is a self-contained apparatus that is co-located with the equipment being analyzed. The apparatus comprises an analyzer computer, one or more sets of sensors connected to the analyzer computer, one or more computer programs executing on the internal computing processors of the analyzer computer, and one or more communication mechanisms between the analyzer computer and external devices such as other computers, equipment, and alarms.

The sensors may include, but are not limited to, sensors for: pressure, flow rate, electrical current, fluid level, acceleration, vibration, valve position, temperature, voltage, pH, hydrogen sulfide, and other sensors of chemicals in the liquid or air. These sensors may be independently supplied with, and sampled by, the present invention only, or they may be shared with the existing fluid distribution equipment control system.

The analyzer computer comprises one or more computing processors, electronic memory, electronic storage for computer programs and files, sensor interfaces to communicate with sensors, digital input and output interfaces to receive and send binary data, a mechanism that provides accurate time, ambient environment sensors, and interfaces to communicate with external devices. The analyzer computer is designed specifically for performance analysis of equipment.

The invention is designed to communicate with external devices for the purpose of user interaction, status reporting, alarm notification, and retrieval of stored data from the analyzer computer. The external devices may consist of one or more commercially available devices. Examples of such devices include, but are not limited to, laptop personal computers, desktop personal computers, smart phones, tablet computers, equipment controllers, computer servers, or a network of computer servers.

The communication mechanisms between the invention and the external devices can be any of the existing standard communication technologies between computers. These standard communication technologies include but are not limited to: discrete digital lines, serial, USB, Wi-Fi, Bluetooth, ZigBee, infrared, Ethernet, telephone, cellular, the Internet, or a composite computer network comprised of a subset of these communication technologies. Whatever the communication mechanism is, both the invention and external devices must include the appropriate interface hardware.

The computer program for the invention resides in the electronic storage of the analyzer computer. When power is applied to the analyzer computer, the computer program runs in the one or more of the internal processors. The computer program periodically requests and receives sensor values from the sensors, uses the sensor values to compute the performance values, analyzes the performance according to internal algorithms, records the results of the analyses in data files in the analyzer computer's electronic storage, sends reports and alarms to external devices and equipment, processes requests to retrieve the stored data files, and sends real-time data and analyses to external devices for display to the user.

The invention is configured to analyze a specific type of fluid distribution equipment, such as a pump station or a pressure reducing valve, when power is applied. The invention will apply a specific set of performance criteria for that type of equipment. By changing the configuration prior to startup, it can be tailored to a different type of equipment.

The sensor values that the computer program in the analyzer computer requests and receives include, as appropriate for the equipment being monitored: pressure, flow rate, electrical current, fluid level, acceleration, vibration, valve position, temperature, humidity, voltage, pH, hydrogen sulfide, and other measures of chemicals in the liquid or air. The computer program in the analyzer computer also requests and receives the value of digital inputs, which indicate the on and off state, or other binary status, of various equipment.

Performance analysis of the equipment is performed in real time by the invention. Performance values are examined as they are computed or compared over a time period specified by the user. Performance analysis values include, as appropriate for the equipment being monitored: minimum, maximum, average, and median of sensor values; equipment power; equipment energy usage; equipment duty cycle; equipment efficiency; flow velocity; differential pressure of liquids; and differential level of liquids. Raw sensor data are not recorded. Instead, a summary of the performance values are recorded in the analyzer computer's electronic storage. Decisions about the performance of the equipment are made based on a set of rules specific to the equipment. These include, but are not limited to, sensor values that exceed user-specified limits; the occurrence of transients (rapid value change) in sensor values and the duration, minimum, and maximum sensor values during each transient; changes over time; and decisions based on conditions specified by the user or learned by the system over time.

The invention will send the equipment status to the user by email, text message, or an output digital signal which can activate a warning signal or provide feedback to a controller. Additional analyses can be performed by other devices that the analyzer apparatus communicates with. Optional software specifically designed for the user to interact with the analyzer apparatus is provided, but is not necessary for the functioning of the apparatus.

BRIEF DESCRIPTION OF THE SEVERAL VIEWS OF THE DRAWING

Preferred embodiments of the invention are shown in the drawings, wherein.

DETAILED DESCRIPTION OF THE INVENTION

Figure 1:
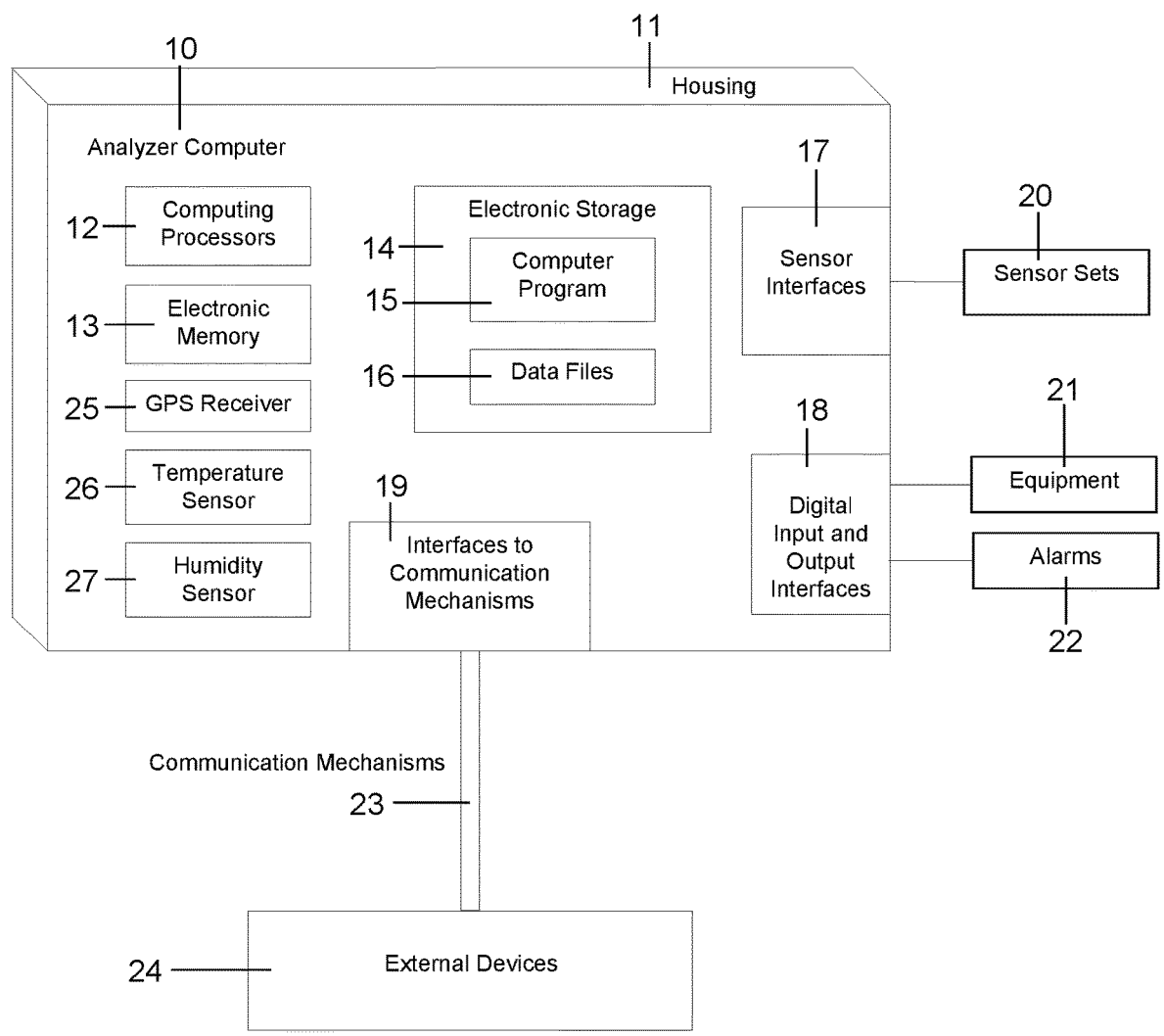
FIG. 1 is an overview of the apparatus for analyzing the performance of fluid distribution equipment.

FIG. 1 is an overview of the apparatus for analyzing the performance of fluid distribution equipment. The apparatus includes: an analyzer computer 10, sensor sets 20 connected to the analyzer computer, a computer program 15 contained in the analyzer computer, digital input and output interfaces 18 from and to various equipment 21 and alarms 22, and communication mechanisms 23 to one or more external devices 24.

The analyzer computer 10 is designed to analyze the performance of equipment by sampling sensors and digital input at regular intervals and interpreting the resulting data. It is designed to be co-located with the fluid distribution equipment, and is automated in its operation. Because the fluid distribution equipment may be located in environments that are wet, dusty, contain corrosive chemicals, and are hot or cold, the housing 11 of the analyzer computer is constructed to resist corrosion and resist the entry of dust and water into the enclosure, and the electronic components are industrially rated to have a wider operational temperature range than consumer electronics. The analyzer computer 10 comprises one or more computing processors 12 capable of running a computer program 15, electronic memory 13 used by the computing processors while running a computer program, electronic storage 14 for indefinitely storing data files 16 and the computer program 15, sensor interfaces 17 for communicating with the sensors, digital input and output interfaces 18 for receiving and sending digital data, interfaces to the communication mechanisms 19, a global positioning system (GPS) receiver 25 for accurate time and location, and a temperature sensor 26 and a humidity sensor 27 for ambient environment sensing.

The computing processors 12, electronic memory 13, and electronic storage 14, are commercially available electronic components. Numerous options exist for these components. Examples include, but are not limited to, ARMV4I processors for the one or more processors 12, DRAM for the electronic memory 13, and flash memory for the electronic storage 14. The sensor interfaces 17 are constructed from commercially available electronic components that include, but are not limited to: parallel digital inputs, analog to digital converters, RS485 serial input/output, and Ethernet. The sensor interfaces 17 that are used depend upon what is required by the specific sensors 20. The digital input and output interfaces 18 are constructed from commercially available electronic components. The components of the analyzer computer described in this paragraph are commercially available and well understood by those skilled in the art, and they are not described further in this document.

The analyzer computer 10 contains one or more interfaces to the communication mechanisms 19. The interfaces to the communication mechanisms 19 will depend upon the types of the communication mechanisms 23 used. The communication mechanisms 23 include, but are not limited to: digital lines, serial, USB, Wi-Fi, Bluetooth, ZigBee, infrared, Ethernet, telephone, cellular, the Internet, or a composite computer network comprised of a subset of these communication mechanisms. Examples of interfaces to the communication mechanisms 19 include, but are not limited to: parallel discrete digital lines, RS232 or RS485 serial adapter, USB adapter, Wi-Fi adapter, Bluetooth adapter, ZigBee adapter, IRDA infrared adapter, Ethernet adapter, telephone modem, and cellular modem. Any one of these interfaces could be used to gain access to an individual external device 24, to the Internet, or to a composite network. The components of the analyzer computer described in this paragraph are commercially available and well understood by those skilled in the art, and they are not described further in this document.

The analyzer computer 10 contains a global positioning system (GPS) receiver 25 to maintain accurate time and location, a temperature sensor 26, and a humidity sensor 27, which are all commercially available electronic components. The accurate time provided by the GPS receiver 25 enables time comparison between results that occur in the invention and events that occur in other equipment. The temperature sensor 26 and humidity sensor 27 are used to monitor for environmental conditions that can cause problems in fluid distribution equipment.

Figure 2:
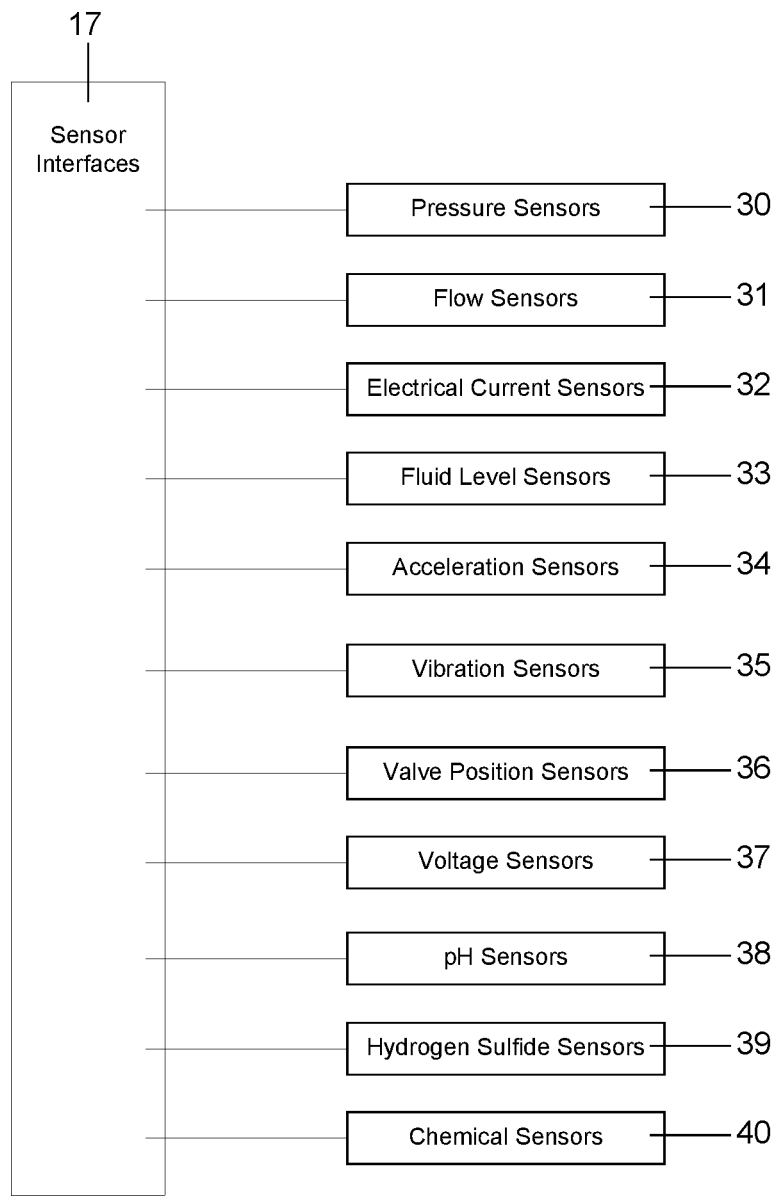
FIG. 2 shows the sensor sets.

FIG. 2 shows the sensor sets. The sensor sets comprise pressure sensors 30, flow sensors 31, electrical current sensors 32, fluid level sensors 33, acceleration sensors 34, vibration sensors 35, valve position sensors 36, voltage sensors 37, pH sensors 38, hydrogen sulfide sensors 39, and chemical sensors 40. The actual sensors that are included in the sensor sets will depend upon the specific fluid distribution equipment that is being analyzed, and the type of analysis being performed. For example, a hydrogen sulfide sensor would be included when analyzing odor control equipment in a sewage treatment plant, but would not be included in a fresh water pumping station.

The purpose of the sensors is as follows. Pressure sensors 30 measure fluid pressure in pipes and vessels to determine if pressure exceeds the rated pressure limits of the equipment. Flow sensors 31 measure the flow rate of fluid through pipes to determine if flow rate exceeds the flow rate limits of any of the fluid distribution equipment. Decreasing flow rate can also provide evidence of equipment degradation, while a sudden increase in flow rate can provide evidence of a rupture or leak in the equipment. Electrical current sensors 32 measure the electrical current flow to pumps, valves, and other equipment. Voltage sensors 37 measure voltage to that equipment. When current is combined with estimated voltage, or with measured voltage from the voltage sensors 37, power and energy usage can be computed. Analyzing the current and voltage can determine the quality of the power entering the equipment. Power and energy usage patterns can be analyzed to improve operational procedures of the fluid distribution equipment. Power and energy usage trends can provide evidence of equipment degradation. Fluid level sensors 33 measure the level of the fluid in tanks and other containment vessels. This information is used to determine when the fluid level exceeds or falls below a safe or effective level. Acceleration sensors 34 and vibration sensors 35 detect and measure rapid motion in pipes, tanks, pumps, and valves. Such motion should be minimal, and when it exceeds a limit it is an indication that there is a problem with the equipment. Valve position sensors 36 measure the degree of restriction of valves. Valves changing position too rapidly can cause a rapid and potentially damaging change in pressure. A closed valve can lead to excessive pressure in front of it. pH sensors 38 measure the pH of the fluid and are an indicator of water quality. Hydrogen sulfide sensors 39 measure the level of this chemical in the air. They are used to determine the effectiveness of odor control equipment. They are also used to detect when this chemical exceeds safe limits for humans. Other chemical sensors 40 such as chlorine sensors and volatile organic compound sensors are used to detect unsafe levels of these chemicals, and can also indicate a leak or equipment failure.

The digital input and output interfaces 18 are connected to equipment 21 and alarms 22. A digital input from equipment 21 comes into the analyzer computer 10 on an individual line or wire, where the value is either 1 or 0. Depending on what the digital input line is connected to, the 1 or 0 value can be interpreted as, but is not limited to: power on or off, a value above or below a threshold, a switch set to a specific value or location, or a physical component of the equipment in a specific position. The digital output can be sent to alarms 22 such as lights or buzzers, to turn them on or off when the analyzer computer 10 detects a particular condition. The digital output can also be sent to equipment 21 when the analyzer computer 10 detects a particular condition. For example, a digital output line to a pump could be changed from 0 to 1 when flow exceeds a threshold. The pump could then decide whether or not to reduce its speed.

Figure 3:
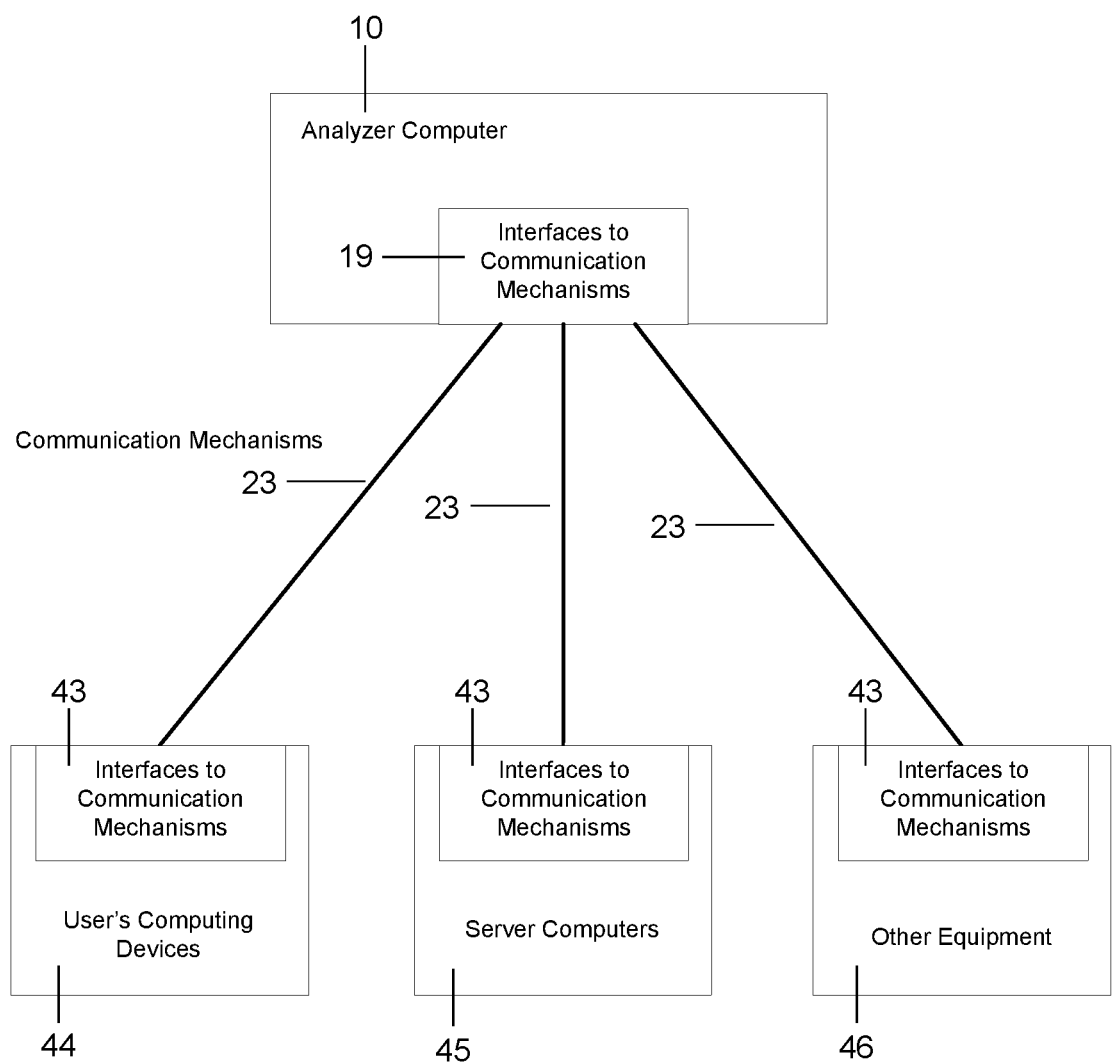
FIG. 3 shows examples of external devices communicating with the analyzer computer.

FIG. 3 shows examples of external devices 44-46 communicating with the analyzer computer 10. These examples include, but are not limited to, user's computing devices 44, server computers 45, and other equipment 46. The analyzer computer 10 communicates with the external devices 44-46 through its interfaces to the communication mechanisms 19. The external devices 44-46 each have corresponding interfaces to communication mechanisms 43. The communication mechanisms 23 and the interfaces to communication mechanisms 19 and 43 are commercially available and understood by those skilled in the art, and they are not described further in this document. At any time, the analyzer computer 10 may be communicating with one or more external devices 44-46, or it may not be communicating with any external devices.

The analyzer computer 10 is co-located with the fluid distribution equipment that it is analyzing. The location may be difficult or impossible for humans to physically access on a regular basis. To overcome this difficulty, the analyzer computer 10 contains one or more interfaces to communication mechanisms 19. One purpose of the interfaces 19 is to provide a means for user's computing devices 44, for example, but not limited to, a personal computer or smart phone, to interact with the analyzer computer 10. The user's computing devices 44 contain an interface to the communication mechanism 43 so that they and the analyzer computer 10 can establish a communication channel with each other. They do this using a commercially available communication mechanism 23, for example, but not limited to, Ethernet, Wi-Fi or the Internet. The user's computing devices 44 contain a software program that uses the communication channel to receive live data from the analyzer computer 10, and request and receive data files 16 from the analyzer computer 10. The software program on the user's computing devices 44 also provides a human-machine interface to display live data and analysis results to the human user, and provides a human-machine interface to allow the human user to change various thresholds and parameters on the analyzer computer 10. Software programs to retrieve and display data, and to change thresholds and parameters on a device, are understood by those skilled in the art, and they are not described further in this document. The communication mechanisms 23 allow a human user to interact with the analyzer computer 10 from any location, including, but not limited to, immediately adjacent using Ethernet or Wi-Fi, to thousands of miles away using the Internet.

The analyzer computer 10 uses its interfaces to the communication mechanisms 19 to connect to server computers 45 for the purpose of sending status messages, warnings, and alerts to human users. These messages can be, but are not limited to, emails, text messages, and application specific alerts or alarms in software programs.

The analyzer computer 10 uses its interfaces to the communication mechanisms 19 to connect to other equipment 46 in the fluid distribution system. Such other equipment 46 may contain sensors, where the sensor data can be retrieved by connecting to the other equipment 46 via, for example, but not limited to, Ethernet, serial, or Wi-Fi communication mechanisms 23. The analyzer computer 10 will analyze the fluid distribution system and may send feedback to the other equipment 46 via, for example, but not limited to, Ethernet, serial, or Wi-Fi communication mechanisms 23. For example, when flow rate exceeds a limit, the analyzer computer 10 could send that information to a pump. The pump could then decide whether or not to alter its speed. The analyzer computer could send warnings to an alarm system that is a component of the fluid distribution system, via its interfaces to the communication mechanism 23.

Figure 4:
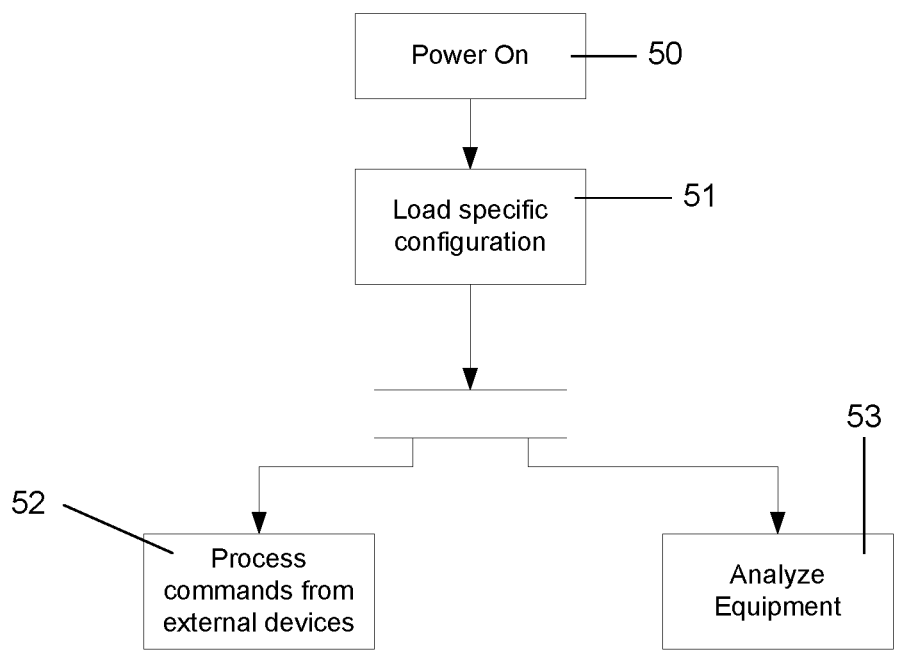
FIG. 4 shows the computer program running in the analyzer computer.

The computer program 15, shown in FIG. 4, starts running in the one or more computer processors 12 when power is applied to the analyzer computer 50. After performing diagnostic tests, the computer program 15 loads a configuration for the specific application being run 51, from the analyzer computer's 10 electronic storage 14. This configuration includes the specifics of the program behavior, the specifics of the sensors in use, and the initial set of limits and rules for analysis of the equipment. The computer program runs continuously while power is applied.

Two concurrent tasks run while the computer program executes. The first task listens for commands from the external devices 52 using one or more of the interfaces to the communication mechanisms 19. This task processes commands that include, but are not limited to: requests for real-time readings from the apparatus, requests for summaries of the equipment analysis, and requests to retrieve stored data files 16. The second concurrent task 53 continually analyzes the performance of the specific equipment for which the apparatus is currently configured.

Figure 5:
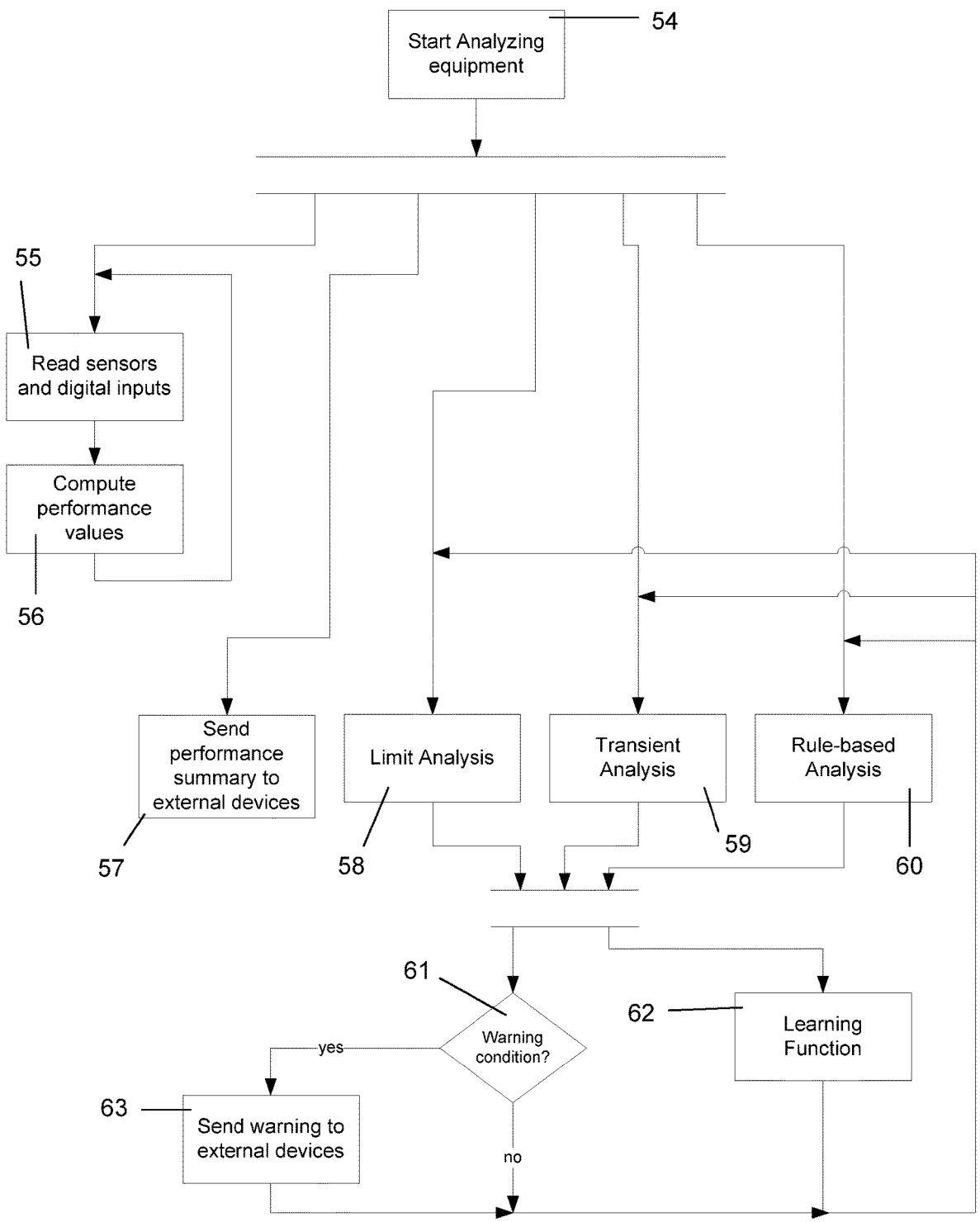
FIG. 5 shows the steps in the computer program that analyze equipment.

FIG. 5 shows the operation of the task that analyzes the equipment. This task starts 54 after the configuration has been loaded for the current application 51. Five independent, concurrent tasks comprise the equipment analysis function of the computer program. The first task reads the sensors and digital inputs at a high sampling rate 55. The raw samples are used to compute the performance values 56, but are not recorded in a data file. The performance values are computed 56 using the raw samples and the digital inputs to reduce the amount of data that needs to be processed further. The performance values computed are specific to the type of equipment for which the apparatus is currently configured. These include, but are not limited to: pressure, flow rate, electric current, voltage, temperature, pH, hydrogen sulfide, vibration, valve position, digital inputs, power, energy consumed, pump efficiency, fluid velocity, machinery run time, machinery idle time, duty cycle, and differential pressure. Computation of these values on computers utilizes techniques that are familiar to someone skilled in the art, and will not be described further here. The results of these computations are internally available to the other tasks in the computer program.

The other four independent, concurrent tasks use the performance values to perform different parts of the equipment analysis. One of the concurrent tasks 57 sends a summary of the performance values to one or more external devices 24 on a predetermined schedule using the interface to the communication mechanisms 19. The performance summary includes, but is not limited to: statistics of the sensor measurements over the predetermined time period including minimum, maximum, mean, and median. The summary also includes the changes in the digital signals and their times of occurrence. This task also writes the summary of performance to data files 16 in the electronic storage 14. The performance values are sent and recorded at a much slower rate than the sampling rate.

Figure 6:
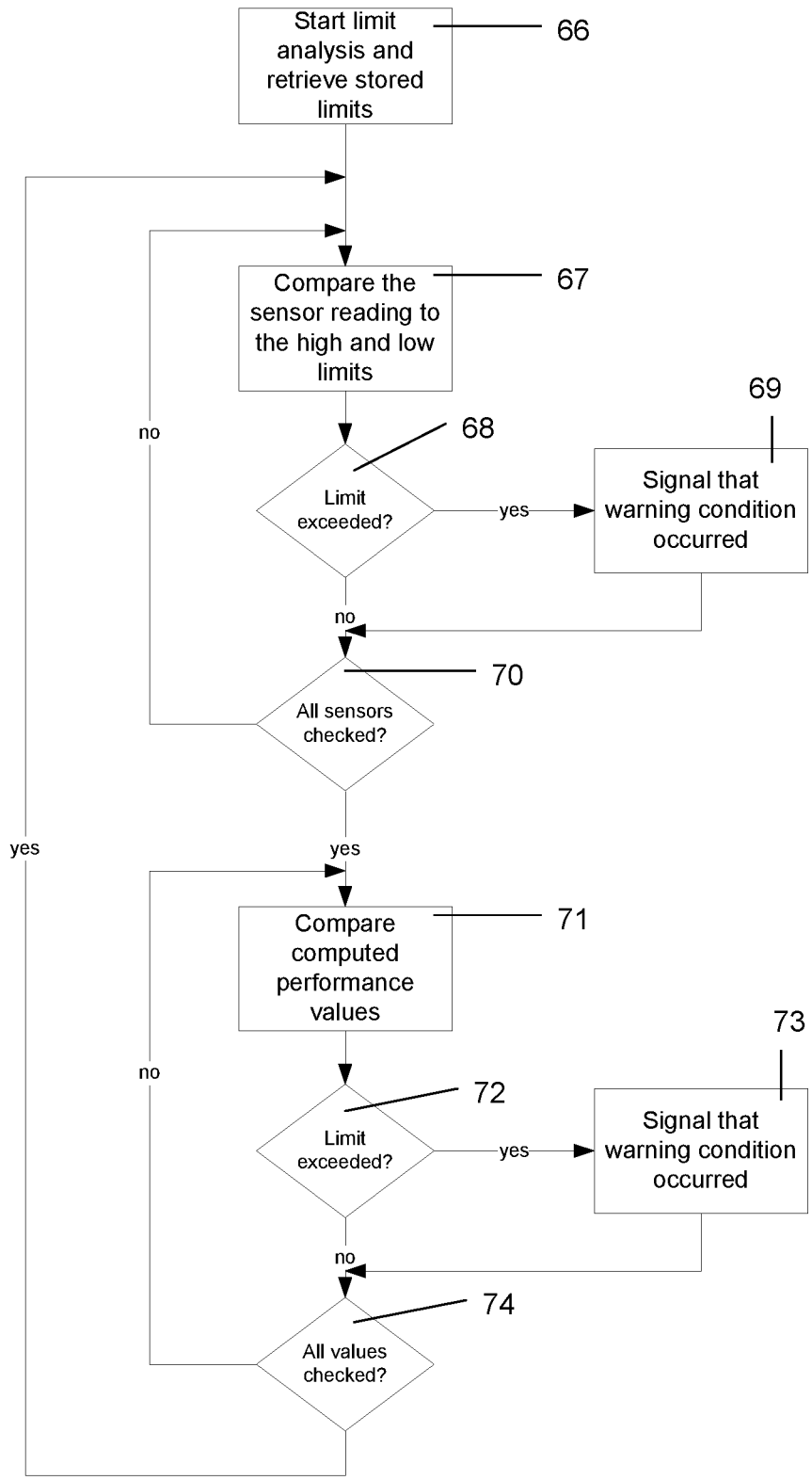
FIG. 6 shows the steps in the computer program that perform the limit analysis.

Another concurrent task analyzes the performance values 58 relative to predefined or learned limits. This is shown in FIG. 6. The task starts by retrieving the stored limits from the configuration for the current application 66. The current reading of a sensor is compared relative to its specified limits 67. If a limit has been exceeded 68, a signal is set internally that indicates which sensor exceeds its limit, when it occurred, and the value that caused the warning 69. The process is repeated for all of the sensors in use 70. The value of a computed performance measurement is compared relative to its limits 71. If a limit has been exceeded 72, a signal is set internally that indicates which computed performance value exceeds its limit, when it occurred, and the value that caused the warning 73. The process is repeated for all of the sensors in use 74. The Limit Analysis process repeats itself as long as power is applied to the apparatus.

Transient sensor events are often an indication that there is a problem in the equipment being analyzed. Transient events are rapid changes in the property being measured.

Figure 7:
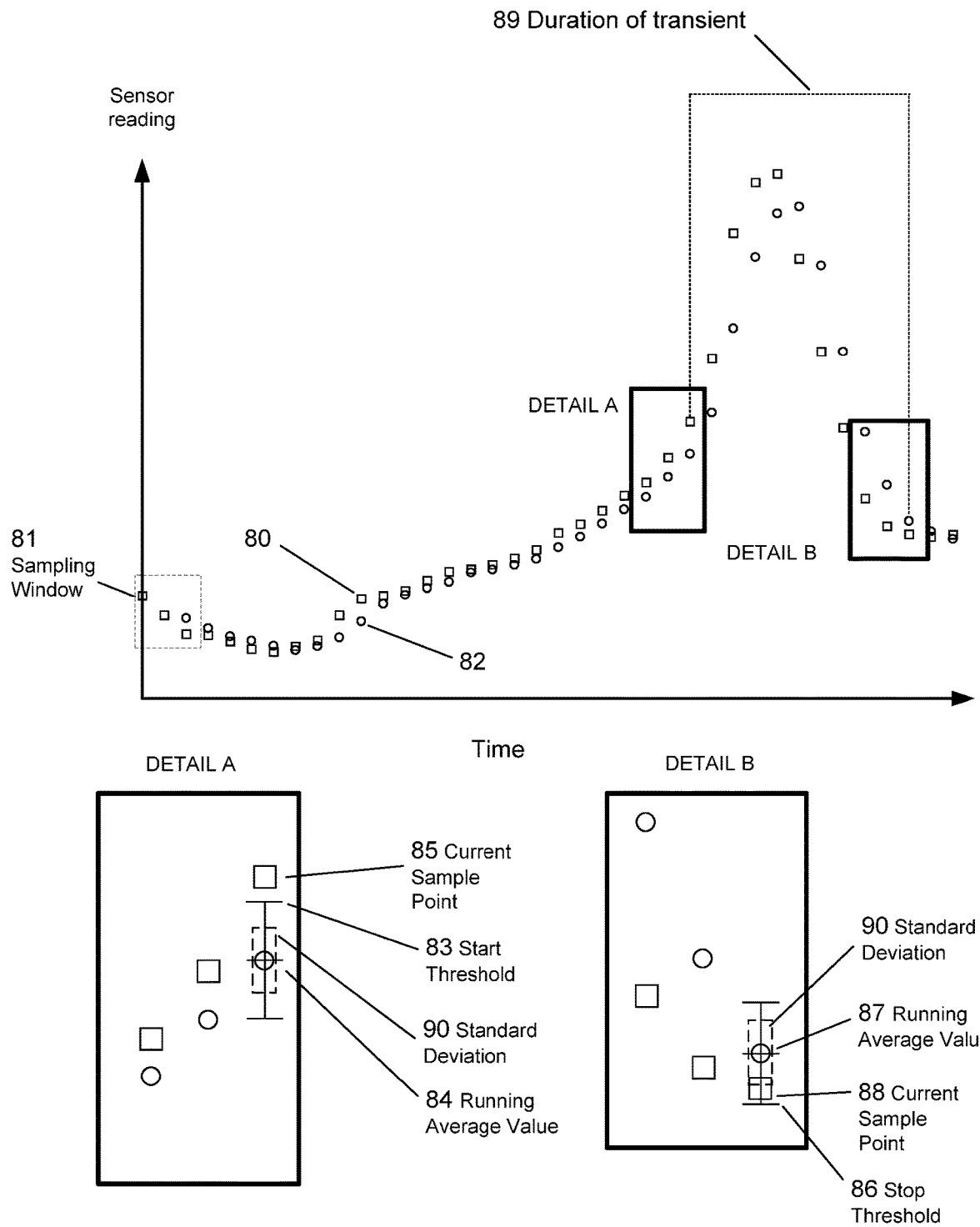
FIG. 7 shows the parameters that determine a transient signal.

These can occur in any of the analog measurements. For example, a pressure transient can cause premature failure of pipes and other fluid handling equipment. A voltage transient can cause the failure of electrical components and interrupt the operation of control systems. In the invention, a transient event is defined as a significant and rapid change in the signal, as shown in FIG. 7.

The analog properties of the equipment's operation will change continuously as the equipment runs. FIG. 7 shows a typical segment of the signal from one of the sensors. The apparatus samples the analog signals from the sensors at discrete intervals in time 80. For the purpose of identifying transient events, the apparatus ignores the actual value of the signal. A running average over a finite time period, referred to here as a "sampling window", is used as the reference for detecting transients 81. This sampling window includes the current sample and some number of previous samples. For each current sample point there is a value corresponding to the running average of all of the points in the sampling window 82. Standard deviation is a commonly used statistic for determining the difference from the norm. The standard deviation for all of the points in the sampling window is computed. Computing statistics on computers utilizes well known techniques, and will not be described further here.

To determine if the current sample is the beginning of a transient, its absolute distance from the running average value is computed. This distance is compared to the start threshold 83 which is the product of the standard deviation 90 and a "deviation multiplier". This deviation multiplier is either predefined or learned as the apparatus runs. As shown in DETAIL A of FIG. 7, the sample 85 has a distance value greater than the start threshold when compared to the corresponding running average value 84. Once the transient event begins, the apparatus will compare each point to the stop threshold 86, which is computed similarly to the start threshold. As shown in DETAIL B of FIG. 7, if the distance value of the current sample 88, compared to the corresponding running average value 87, is less than the stop threshold, the transient event is ended. At the end of the transient event, its time of occurrence, duration 89, maximum and minimum values, and standard deviation are computed.

Figure 8:
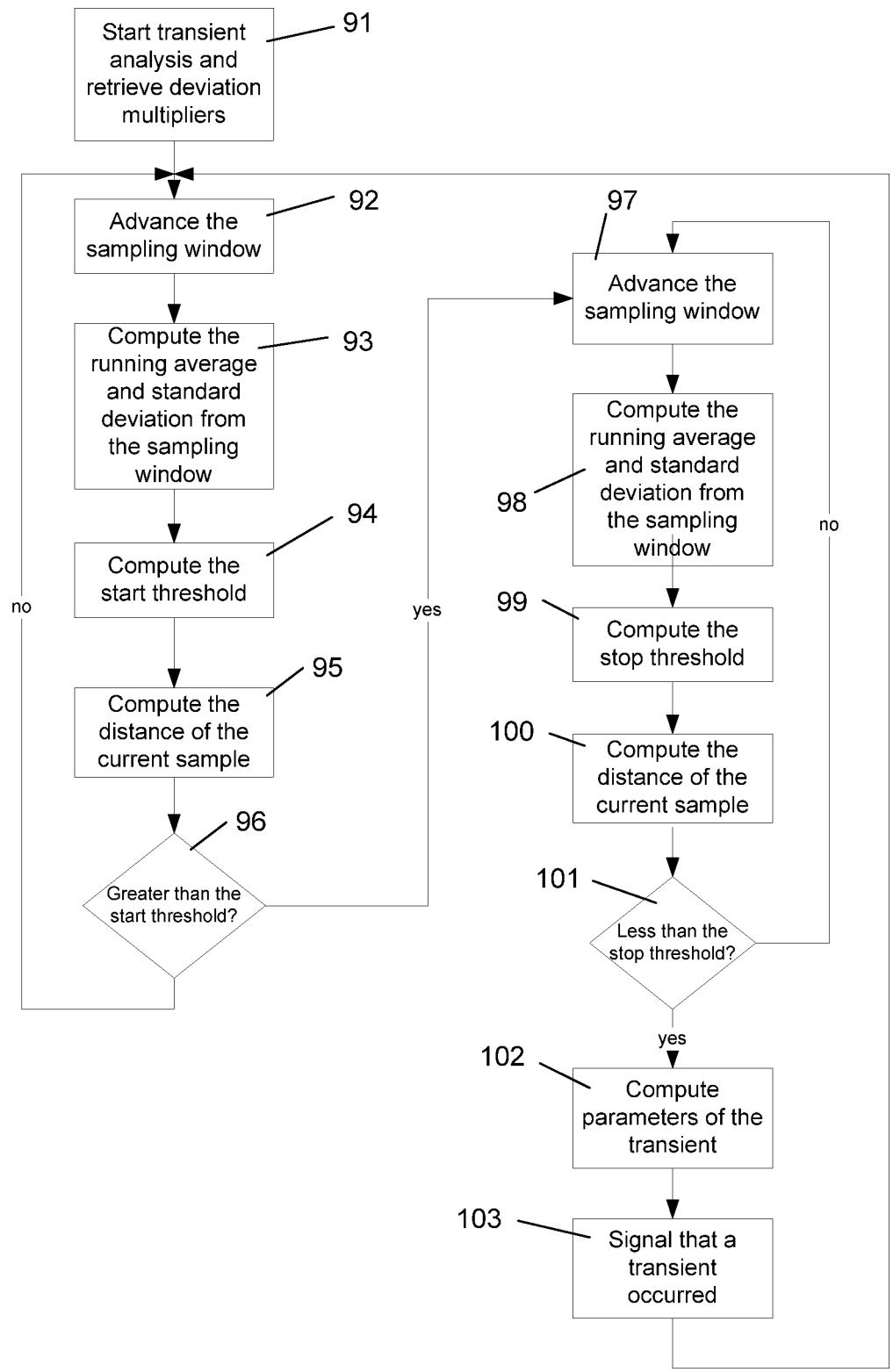
FIG. 8 shows the steps in the computer program that perform the transient analysis.

Another of the concurrent tasks shown in FIG. 5 examines the processed sensor readings to detect transients 59. The transient analysis task is shown in FIG. 8. The task starts by retrieving the predefined or learned deviation multipliers from the configuration for the current application 91. The sampling window of previous samples, to be used for computing the running average and standard deviation, is advanced to include the current sensor reading 92. The average of these samples and their standard deviation is computed 93. The start threshold is computed by multiplying the standard deviation with the deviation multiplier for the start threshold 94. The distance from the current sample to the running average is computed 95. If this distance is not greater than the start threshold 96, the loop continues 92. If this distance is greater then the start threshold, a transient is detected and the program continues on a different path. The running window is advanced 97, the running average and standard deviation are computed 98, the stop threshold is computed by multiplying the standard deviation with the deviation multiplier for the stop threshold 99, and the distance from the current sample to the running average is computed 100. If this distance is not less than the stop threshold 101, the loop continues 97. If this distance is less than the stop threshold, the transient is ended and the minimum, maximum, and duration of the transient are computed 102. A signal is set internally to indicate that a transient was detected 103. The process continues to look for the start of the next transient 92. The transient analysis process repeats itself as long as power is applied to the apparatus.

Figure 9:
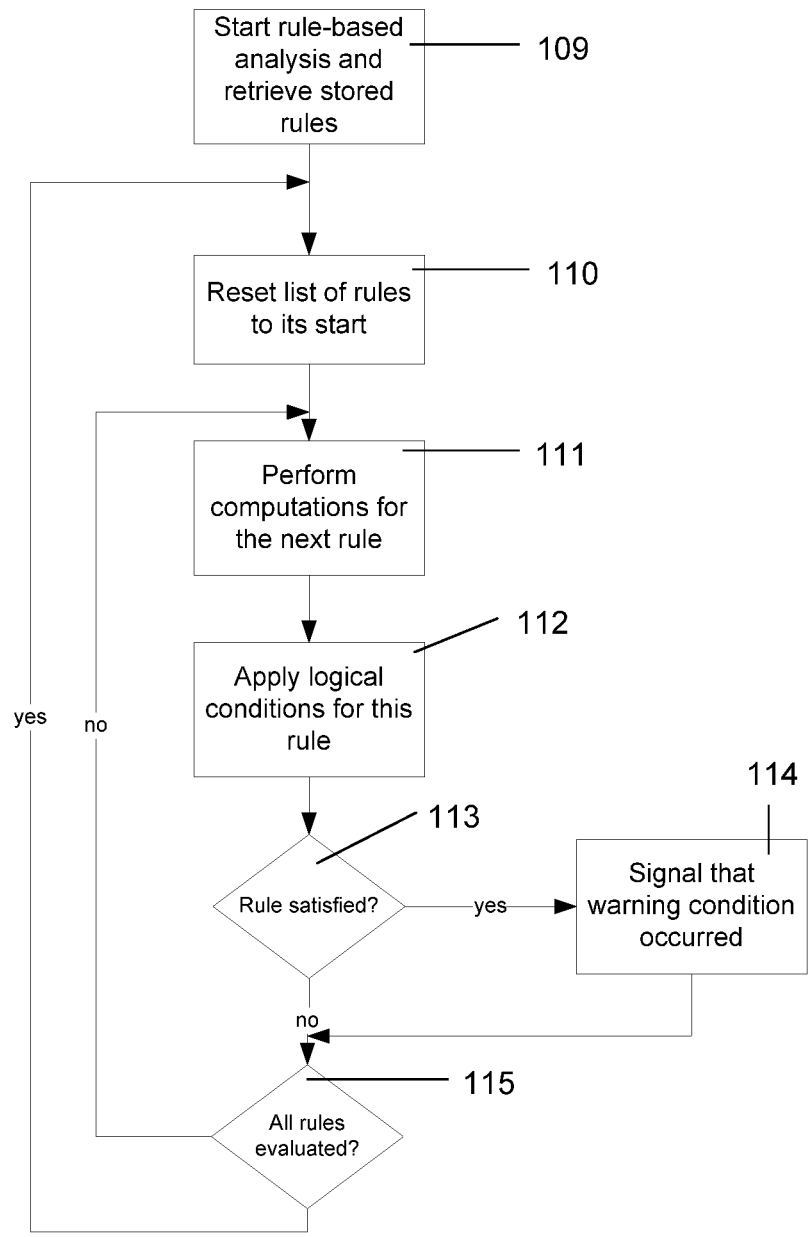
FIG. 9 shows the steps in the computer program that perform the rule-based analysis.

The last of the concurrent tasks that are shown in FIG. 5 implements rules for warning conditions that combine sensor readings and other performance values 60. A rule may be the result of a function applied to one or more computed performance values, such as the product of flow rate and pressure. Logical conditions may then be applied to the result of this computation, a transient, or a limit, such as if the electric current limit is exceeded only during daylight hours. This rule-based analysis task is shown in FIG. 9. The task starts by retrieving the predefined and learned rules from the configuration for the current application 109. The list of rules is reset 110 to its beginning. The next rule is considered by performing the necessary computations 111. Logical conditions for the next rule are applied 112. If this rule has been satisfied 113, a signal is set internally that indicates which rule caused a warning and when it occurred 114. The process is repeated for all of the rules in the list for this application 115. The rule-based analysis process repeats itself as long as power is applied to the apparatus 110. The representation and application of rules in computer programs utilizes well known techniques, and will not be described further here.

The limit analysis, transient analysis, and rule-based analysis tasks shown in FIG. 5 run concurrently and independently, and make their results available internally to other tasks. One task processes these results to determine if warnings need to be sent to external devices 61. These warnings are sent to external devices using one or more of the communication mechanisms 63. For example, email and text messages are sent to user's personal computers and phones. Digital signals are sent to alarm devices and other equipment. Modbus messages are sent to equipment controllers and other supervisory programs.

A separate, independent task examines the results of the analyses, and attempts to modify the criteria for determining a warning 62. The learning function takes into account the time and frequency of occurrence of the warnings to refine the parameters of the analysis routines. In this preferred embodiment, a histogram of the occurrence of transients is maintained relative to the time of day and day of the week. From this histogram, the deviation multipliers can be adjusted to eliminate false positive warnings and to adjust for patterns of usage. This embodiment uses this histogram technique to adjust the limits on the performance values to ignore random, infrequent variations. This and other learning functions can be implemented using well known techniques, and will not be described further here.

As will be understood by those skilled in the art, many changes in the apparatus and methods described above may be made by the skilled practitioner without departing from the spirit and scope of the invention, which should be limited only as set forth in the claims which follow.

We claim:

1. A performance analysis apparatus for fluid distribution equipment that operates independently of the control system of said fluid distribution equipment to automatically determine when said equipment is not functioning correctly, comprising:

an analyzer computer comprising one or more computing processors for running computer programs, an electronic memory used by said analyzer computer while running a computer program, a mechanism that provides accurate time, an electronic storage for indefinitely storing data files and computer programs, and sensor interfaces for connection to sensor sets;

one or more sensor sets, connected to said analyzer computer via said sensor interfaces, comprising one or more sensors for measuring physical properties of zero or more pipes, zero or more pumps, zero or more valves, zero or more wells, zero or more filters, and zero or more fluid storage vessels, and connections to said sensor interfaces of said analyzer computer;

a computer program stored in said electronic storage and running in said computing processors that manages the functions of said performance analysis apparatus;

wherein said analyzer computer, said sensor sets, and said computer program are co-located with the equipment being analyzed;

whereby said computer program reads configuration data from data files to determine the types of fluid distribution equipment that are being collectively analyzed and the sensor sets that are present; repetitively receives raw physical measurements from said sensor sets; computes the physical properties of said fluid distribution equipment from said raw physical measurements; computes limit analysis to determine if said physical properties exceed limits; computes transient analysis to detect transient events in said computed physical properties, and for each said transient event computes the start time and duration of said transient event, and computes the minimum and maximum physical property values during said transient event; computes rule-based analysis by using a set of rules where each rule performs specific computations on said physical properties, and applies logic operations on the results of said computations, to determine if said fluid distribution equipment is not functioning properly; stores the results of said computations and times of receipt of said raw physical measurements used in said computations in said electronic storage so that the number of results that are stored is limited only by the size of said electronic storage: performs a learning function that uses time and frequency of occurrence of anomalies detected during said limit analysis and said transient analysis and said rule-based analysis to refine the parameters in said limit analysis and in said transient analysis and in said rule-based analysis, so that said computer program adapts over time to more accurately perform said limit analysis and said transient analysis and said rule-based analysis, and adjusts to patterns of usage of said fluid distribution equipment.

2. The performance analysis apparatus according to claim 1, wherein said analyzer computer further comprising a communication mechanism for exchanging commands and data between said analyzer computer and one or more external devices whereby said computer program communicates with said external devices to receive commands and settings, send data, and receive data.

3. The performance analysis apparatus according to claim 1, wherein said analyzer computer further comprising digital input and output interfaces whereby said computer program receives binary values from said fluid distribution equipment which said computer program uses in its computations, and said computer program sends binary values to said fluid distribution equipment.

4. The performance analysis apparatus according to claim 1, wherein said analyzer computer further comprising ambient environment sensors whereby said computer program includes them in the processing of the sensor set.

5. The performance analysis apparatus according to claim 4, wherein said ambient environment sensor is a temperature sensor.

6. The performance analysis apparatus according to claim 4, wherein said ambient environment sensor is a humidity sensor.

7. The performance analysis apparatus according to claim 2, wherein said communication mechanism is discrete digital lines.

8. The performance analysis apparatus according to claim 2, wherein said communication mechanism is serial.

9. The performance analysis apparatus according to claim 2, wherein said communication mechanism is USB.

10. The performance analysis apparatus according to claim 2, wherein said communication mechanism is Wi-Fi.

11. The performance analysis apparatus according to claim 2, wherein said communication mechanism is Bluetooth.

12. The performance analysis apparatus according to claim 2, wherein said communication mechanism is Zigbee.

13. The performance analysis apparatus according to claim 2, wherein said communication mechanism is infrared.

14. The performance analysis apparatus according to claim 2, wherein said communication mechanism is Ethernet.

15. The performance analysis apparatus according to claim 2, wherein said communication mechanism is landline telephone.

16. The performance analysis apparatus according to claim 2, wherein said communication mechanism is cellular radio.

17. The performance analysis apparatus according to claim 2, wherein said communication mechanism is the Internet.

18. The performance analysis apparatus according to claim 1, wherein said sensor set comprises a pressure sensor.

19. The performance analysis apparatus according to claim 1, wherein said sensor set comprises a flow rate sensor.

20. The performance analysis apparatus according to claim 1, wherein said sensor set comprises an electrical current sensor.

21. The performance analysis apparatus according to claim 1, wherein said sensor set comprises a fluid level sensor.

22. The performance analysis apparatus according to claim 1, wherein said sensor set comprises an accelerometer.

23. The performance analysis apparatus according to claim 1, wherein said sensor set comprises a valve position sensor.

24. The performance analysis apparatus according to claim 1, wherein said sensor set comprises a voltage sensor.

25. The performance analysis apparatus according to claim 1, wherein said sensor set comprises a pH sensor.

26. The performance analysis apparatus according to claim 1, wherein said sensor set comprises a hydrogen sulfide sensor.

27. The performance analysis apparatus according to claim 1, wherein said sensor set comprises a volatile organic compounds sensor.

28. The performance analysis apparatus according to claim 1, wherein said computer program computes mean, median, maximum, and minimum values of said physical properties, and records the time and said mean, median, maximum and minimum values in said data files.

29. The performance analysis apparatus according to claim 1, wherein said computer program computes the duty cycle of said pumps in said fluid distribution equipment and stores the time and said duty cycle of said pumps in said data files.

30. The performance analysis apparatus according to claim 1, wherein said computer program computes the flow velocity in said fluid distribution equipment and stores the time and said flow velocity in said data files.

31. The performance analysis apparatus according to claim 1, wherein said computer program computes the differential pressure in said fluid distribution equipment and stores the time and said differential pressure in said data files.

32. The performance analysis apparatus according to claim 1, wherein said computer program computes the differential level in said fluid distribution equipment and stores the time and said differential level in said data files.

33. The performance analysis apparatus according to claim 1, wherein said computer program computes the efficiency of said fluid distribution equipment and stores the time and said efficiency in said data files.

34. The performance analysis apparatus according to claim 2, wherein said computer program sends warning and status messages via email.

35. The performance analysis apparatus according to claim 2, wherein said computer program sends warning and status messages via text message.

36. The performance analysis apparatus according to claim 3, wherein said computer program sends binary warning and status output via digital output.

37. The performance analysis apparatus according to claim 1, wherein said computer program maintains a histogram of transient events over time of day and day of week, that said computer program uses to adjust deviation multipliers to eliminate false transients.

* * * * *